US010368739B2

(12) United States Patent
Plaian et al.

(10) Patent No.: US 10,368,739 B2
(45) Date of Patent: Aug. 6, 2019

(54) EYE EXAMINATION APPARATUS

(71) Applicant: CENTERVUE S.P.A., Padua (IT)

(72) Inventors: Andrei Plaian, Ponte San Nicolò (IT); Federico Manzan, San Pietro di Feletto (IT); Marco D'Aguanno, Padua (IT)

(73) Assignee: Centervue S.p.A., Padua (IT)

( * ) Notice: Subject to any disclaimer, the term of this patent is extended or adjusted under 35 U.S.C. 154(b) by 0 days.

(21) Appl. No.: 15/510,011

(22) PCT Filed: Sep. 7, 2015

(86) PCT No.: PCT/EP2015/070397
§ 371 (c)(1),
(2) Date: Mar. 9, 2017

(87) PCT Pub. No.: WO2016/037984
PCT Pub. Date: Mar. 17, 2016

(65) Prior Publication Data
US 2017/0258323 A1 Sep. 14, 2017

(30) Foreign Application Priority Data
Sep. 12, 2014 (IT) .............................. TV2014/A0131

(51) Int. Cl.
*A61B 3/10* (2006.01)
*A61B 3/12* (2006.01)
*A61B 3/14* (2006.01)

(52) U.S. Cl.
CPC .............. *A61B 3/1025* (2013.01); *A61B 3/12* (2013.01); *A61B 3/14* (2013.01)

(58) Field of Classification Search
CPC ............ A61B 3/1025; A61B 3/14; A61B 3/12
(Continued)

(56) References Cited

U.S. PATENT DOCUMENTS 7,331,669 B2    2/2008  Elsner
8,789,950 B2    7/2014  Mensink et al.
(Continued)

FOREIGN PATENT DOCUMENTS

CN    101254090 A    9/2008
CN    103108582 A    5/2013
(Continued)

OTHER PUBLICATIONS

European Patent Office: International Search Report for PCT/EP2015/070397 completed Oct. 19, 2015 (dated Oct. 29, 2015).
(Continued)

*Primary Examiner* — Tuyen Tra
(74) *Attorney, Agent, or Firm* — Patterson Intellectual Property Law, P.C.; Gary L. Montle

(57) ABSTRACT

The present invention relates to an eye examination apparatus comprising an illuminator adapted to project a light beam to illuminate the retina of an eye; an image sensor adapted to receive light reflected by the retina and to acquire images of the retina; scanning means adapted to perform optical scans of the retina moving the light beam projected on the retina along a scanning direction; separation means of the light beams adapted to separate the projected light from the light reflected by the retina and directed toward said image sensor; and a control unit to control the operation of said scanning apparatus. During the operation of said apparatus, in order to acquire each single image of a region of the retina to be framed, said image sensor integrates light reflected by the retina during at least two complete optical scans of said region of the retina by said scanning means.

19 Claims, 8 Drawing Sheets

(58) Field of Classification Search
USPC .................................. 351/200, 205, 206
See application file for complete search history.

(56) References Cited

U.S. PATENT DOCUMENTS

| | | | |
|---|---|---|---|
| 9,936,872 B2* | 4/2018 | Gerrans | ................. A61B 3/14 |
| 2010/0142780 A1 | 6/2010 | Yasuno et al. | |
| 2013/0229620 A1 | 9/2013 | Hammer et al. | |

FOREIGN PATENT DOCUMENTS

| | | |
|---|---|---|
| CN | 103054550 A | 2/2014 |
| EP | 1961374 A1 | 8/2008 |
| EP | 2374404 A1 | 10/2011 |
| JP | S6180215 A | 4/1986 |
| JP | 2005507727 | 3/2005 |
| JP | 2011087830 A | 5/2011 |
| WO | 3962397 A1 | 12/1999 |
| WO | 2013151879 A1 | 10/2013 |

OTHER PUBLICATIONS

State Intellectual Property Office of the People's Republic of China, Notification of First Office Action, dated May 16, 2018, 13 pages.
Japan Patent Office: First Office Action dated May 14, 2019 in corresponding Patent Application No. JP2017513671. (Japanese and English translations).

* cited by examiner

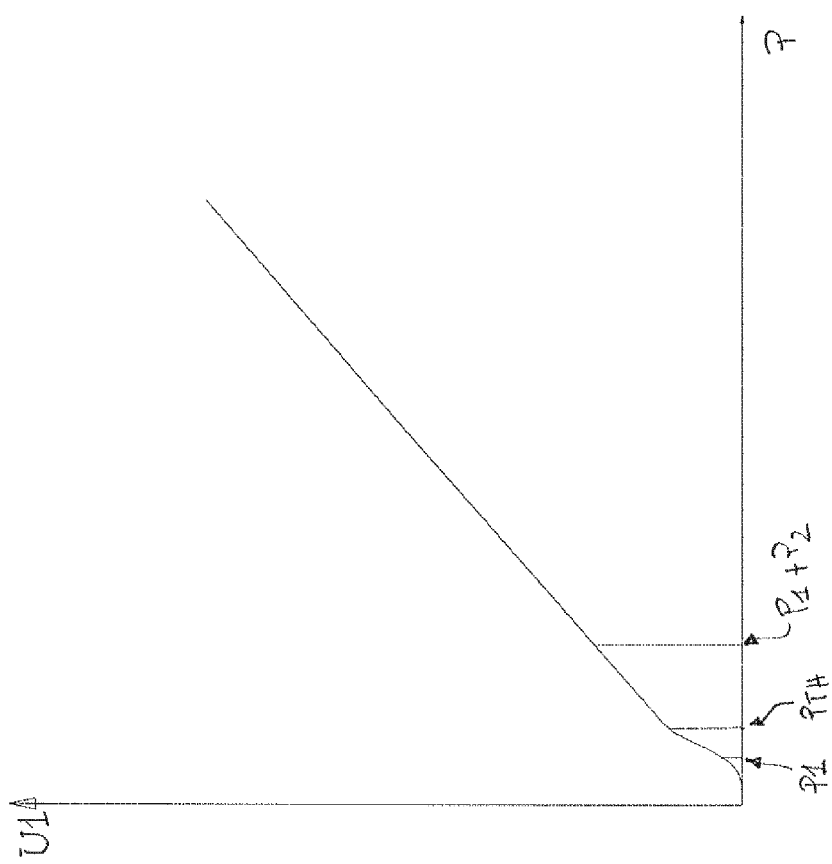

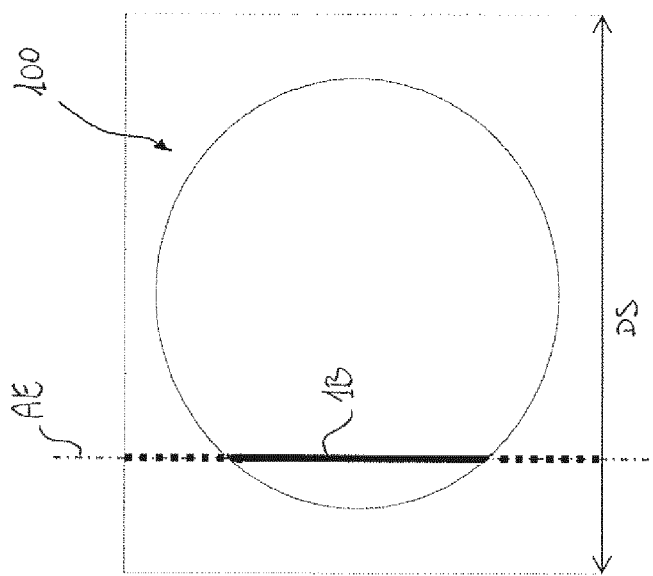

EYE EXAMINATION APPARATUS

BACKGROUND OF THE INVENTION

The present invention relates to an eye examination apparatus.

The use of apparatus for eye examination of confocal type is widely known.

These apparatus are capable of taking photographs and videos of the retina with a good light contrast and relatively large field of view (even greater than 45°) for relatively narrow pupils (i.e. even for pupil diameters of less than 3 mm).

For reasons of simplicity of construction, confocal line scanning eye examination apparatus are of particular industrial and commercial interest.

Examples of confocal line scanning apparatus are described in patents U.S. Pat. Nos. 4,241,257, 7,331,669 and EP2392915A1.

These apparatus scan the retina with a light beam that illuminates a very narrow region of the retina, typically in the form of a line. They collect and de-scan the light reflected by the retina making it pass through a fixed diaphragm provided with a slit that eliminates most of the spurious light coming from undesired reflections. The light passing through the diaphragm is then projected on a sensor which uses the information thus acquired to reconstruct one or more images of the retina.

Prior art confocal line scanning apparatus acquire images of the retina during a single optical scan of the same retina, completed in a predetermined time, typically a few tens of millisecond.

Patent application EP2392915A1 describes, for example, an optical image capturing system that scans an object with a line of light, de-scans the light reflected by the object, passes it through a confocal opening and rescans it to obtain a two-dimensional image, which is then acquired by means of a two-dimensional sensor that uses a frame-rate the same as the scanning frequency.

U.S. Pat. No. 7,331,669 describes a digital photographic system that scans the retina with the light generated by an illuminator containing a diaphragm with an opening in the shape of a slit to reduce undesired reflections. In one of the construction variants proposed, the light reflected by the retina is de-scanned, passed through a confocal diaphragm that eliminates reflections and then rescanned to obtain a two-dimensional image projected on a two-dimensional sensor. The fact that the image of the retina is acquired during a single scan of the retina is evident from the fact that patent U.S. Pat. No. 7,331,669 suggests reducing the scanning frequency of the retina to increase the exposure time of the two-dimensional sensor.

One of the problems of the systems described in the aforesaid patent documents consists in that they do not provide practical solutions for controlling the quantity of light reflected by the retina during acquisition of the images of the same retina. This prevents optimization of the exposure time or the gain of the sensor. The brightness of the images is therefore variable as a function of the reflectivity of the retina and can vary from one subject to another.

To acquire images without controlling the quantity of light reflected by the retina, it is possible to decrease the exposure time or the gain of the sensor to values such as to prevent saturation of the image in the case of very reflective retinas.

The brightness of the images acquired can also be further adjusted by means of processing of the same images after their acquisition (post-processing of the images).

A disadvantage of this solution consists in the fact that the images of retinas with low reflectivity are often too dark and have a low signal/noise ratio.

The brightness of the images can be improved by post-processing of these images. However, this does not significantly improve the signal/noise ratio, which generally remains low.

An alternative solution, which can be used to acquire infrared images, consists in measuring the reflectivity of the retina during acquisition of a video so as to be able to adjust the power of the infrared source or the gain of the sensor before acquiring the final images of the same retina.

However, in the case of scanning with visible light, this technique cannot be used, given that illumination of the retina with an intense visible light would cause the pupil of the eye to close before being able to acquire the final images of the retina.

A known technique to improve the signal to noise ratio is to acquire a certain number of separate images and combine these images in a post-processing procedure, using a computer, to produce a single image with a better signal to noise ratio.

A drawback of this method is represented by the high implementation costs, since it requires expensive high speed camera and acquisition hardware. Consequently, this method is generally used on more expensive point type scanning systems and not on line scanning systems, which usually trade off performance with costs.

This solution is used, for example, in the Heidelberg Noise Reduction™ system adopted by Heidelberg Engineering Inc. in their Spectralis™ OCT products.

Such technique is also used by other eye examination apparatus, especially OCT, as the one disclosed in the patent document EP1961374.

The document WO2012/041723A1 describes a conventional fundus camera with a system for controlling the quantity of light emitted toward the retina of the eye during acquisition of the images.

This system is conceived for a fundus camera that illuminates the whole retina simultaneously by means of a flash of light. It measures the quantity of light reflected by the retina through light sensors and deactivates the illuminator of the fundus camera, when the quantity of reflected light reaches a predetermined threshold.

The document does not provide solutions that make it possible also to apply this solution to a confocal line scanning apparatus.

BRIEF SUMMARY OF THE INVENTION

The main aim of the present invention is to provide an eye examination apparatus, of confocal line scanning type, which solves the aforesaid problems of the prior art.

Within this aim, an object of the present invention is to provide an eye examination apparatus capable of automatically adjusting the quantity of light coming from the retina and directed toward the image sensor.

A further object of the present invention is to provide an eye examination apparatus that is easy to produce on an industrial scale, at competitive costs.

This aim and these objects, together with other objects that will be more apparent from the subsequent description and from the accompanying drawings, are achieved according to the invention by an eye examination apparatus according to claim 1 and to the related dependent claims, proposed hereunder.

In a general definition thereof, the apparatus according to the invention comprises at least an illuminator adapted to project a light beam in an eye to illuminate the retina thereof.

Said light beam is shaped to form a line of light that extends along a main axis of extension, when said light beam intersects the retina.

The illuminator therefore illuminates a portion of retina having the shape of the aforesaid line of light.

The apparatus according to the invention also comprises:
an image sensor adapted to receive light reflected by the retina and to acquire images of the retina;
scanning means adapted to perform optical scans of the retina, cyclically moving the light beam projected by the illuminator on the retina along a scanning direction substantially perpendicular to the main axis of extension of the line of light projected by the illuminator;
separation means of the light beams adapted to separate the light projected by the illuminator from the light reflected by the retina and directed toward said image sensor;
a control unit to control the operation of said apparatus.

According to the invention, during the operation of said apparatus, to acquire each single image of a region of the retina to be framed, said image sensor integrates light reflected by the retina during at least two complete optical scans of the region of the retina to be framed by said scanning means.

Preferably, during the operation of said apparatus, to acquire each single image of a region of the retina to be framed, the image sensor integrates light reflected by the retina during an integer number of complete optical scans of the region of the retina to be framed by said scanning means.

According to the present invention, after having reached an optimal exposure, the sensor delivers one single image at the end of the acquisition process.

It is important to notice that the information received from the retina during multiple scans thereof is combined directly at the level of the image sensor to produce the final image of the retina and not in a post-processing procedure involving a computer, as it occurs in the known state of the art.

Preferably, the apparatus according to the invention comprises:
a light detection device comprising at least a photosensitive element adapted to provide a detection signal indicative of the incident light power;
a beam splitter adapted to divide the light reflected by the retina and passing through said separation means of the light beams into a first portion and second portion of reflected light. The beam splitter directs the first portion of reflected light toward the light detection device and directs the second portion of reflected light toward the image sensor.

Preferably, the apparatus according to the invention comprises signal conditioning means adapted to receive at least a detection signal from said at least a photosensitive element and to provide a measuring signal indicative of the light energy received by at least a photosensitive element.

Preferably, the light detection device comprises a mask adapted to be optically conjugated with the retina. The mask comprises at least an opening adapted to allow the passage of light (included in the aforesaid first portion of light) toward said at least a photosensitive element.

Preferably, the light detection device comprises at least two photosensitive elements arranged according to a first direction optically conjugated with the main axis of extension of the line of light projected by the illuminator on the retina, during the operation of said apparatus.

Preferably, the mask of the light detection device comprises at least two openings arranged according to a second direction optically conjugated with the main axis of extension of the line of light projected by the illuminator on the retina, during the operation of said apparatus.

Preferably, the light detection device comprises at least an emitter operatively associated with said at least a photosensitive element. Said at least an emitter is adapted to project light on said at least a photosensitive element.

Preferably, during the operation of said apparatus, said at least an emitter (that can be activated by said control unit) projects light on said at least a photosensitive element when the illuminator and the image sensor are activated by the control unit, i.e. when the illuminator projects light on the retina and the image sensor receive light reflected by the retina to acquire an image of the same retina.

Preferably, the light detection device comprises a support on which there is mounted said at least a photosensitive element and an intermediate body provided with at least a cavity. The intermediate body is operatively associated with the support and with the mask of the light detection device so that said at least a cavity communicates with said at least an opening of the mask to allow the passage of light toward said at least a photosensitive element and defines a chamber adapted to laterally enclose said at least a photosensitive element.

Preferably, the control unit is capable of controlling the operation of the illuminator based on the measuring signal provided by the signal conditioning means.

Preferably, the control unit is capable of performing a first adjustment procedure of the quantity of light directed toward the image sensor. The aforesaid first adjustment procedure comprises the following steps:
providing control signals to activate the illuminator and the image sensor when the scanning means are in proximity of an end-of-travel position;
acquiring the measuring signal provided by the signal conditioning means;
comparing said measuring signal with a threshold value;
if said measuring signal has values higher than said threshold value, waiting for completion of the optical scan of the retina in progress;
providing control signals to deactivate the illuminator when the optical scan in progress is completed.

Preferably, the control unit is capable of performing a second adjustment procedure of the quantity of light directed toward the image sensor. The aforesaid second adjustment procedure comprises the following steps:
providing control signals to activate the illuminator and the image sensor when the scanning means are in proximity of an end-of-travel position;
acquiring the measuring signal provided by the signal conditioning means, after said scanning means have performed a first integer number N1 of optical scans of said retina;
comparing said measuring signal with a threshold value;
calculating a second integer number N2 of scans still to be performed in the case in which said illuminator is adjusted to a new power value;
providing control signals to change the power of the illuminator to said new power value, when the scanning means are in proximity of an end-of-travel position;
waiting for completion of said number N2 of optical scans of the retina;

providing control signals to deactivate the illuminator when said number N2 of optical scans of the retina is completed.

BRIEF DESCRIPTION OF THE SEVERAL VIEWS OF THE DRAWINGS

Further characteristics and advantages of the eye examination apparatus according to the invention will be more apparent with reference to the description given below and to the accompanying figures, provided purely for explanatory and non-limiting purposes, wherein:

FIG. 7 schematically shows an operating characteristic curve of a photosensitive element that can be used in the eye examination apparatus according to the invention, in the embodiments shown in FIGS. 2-6; and FIG. 8 schematically shows a line of light projected on the retina of an eye by the eye examination apparatus according to the invention.

DETAILED DESCRIPTION OF THE INVENTION

Figure 1:
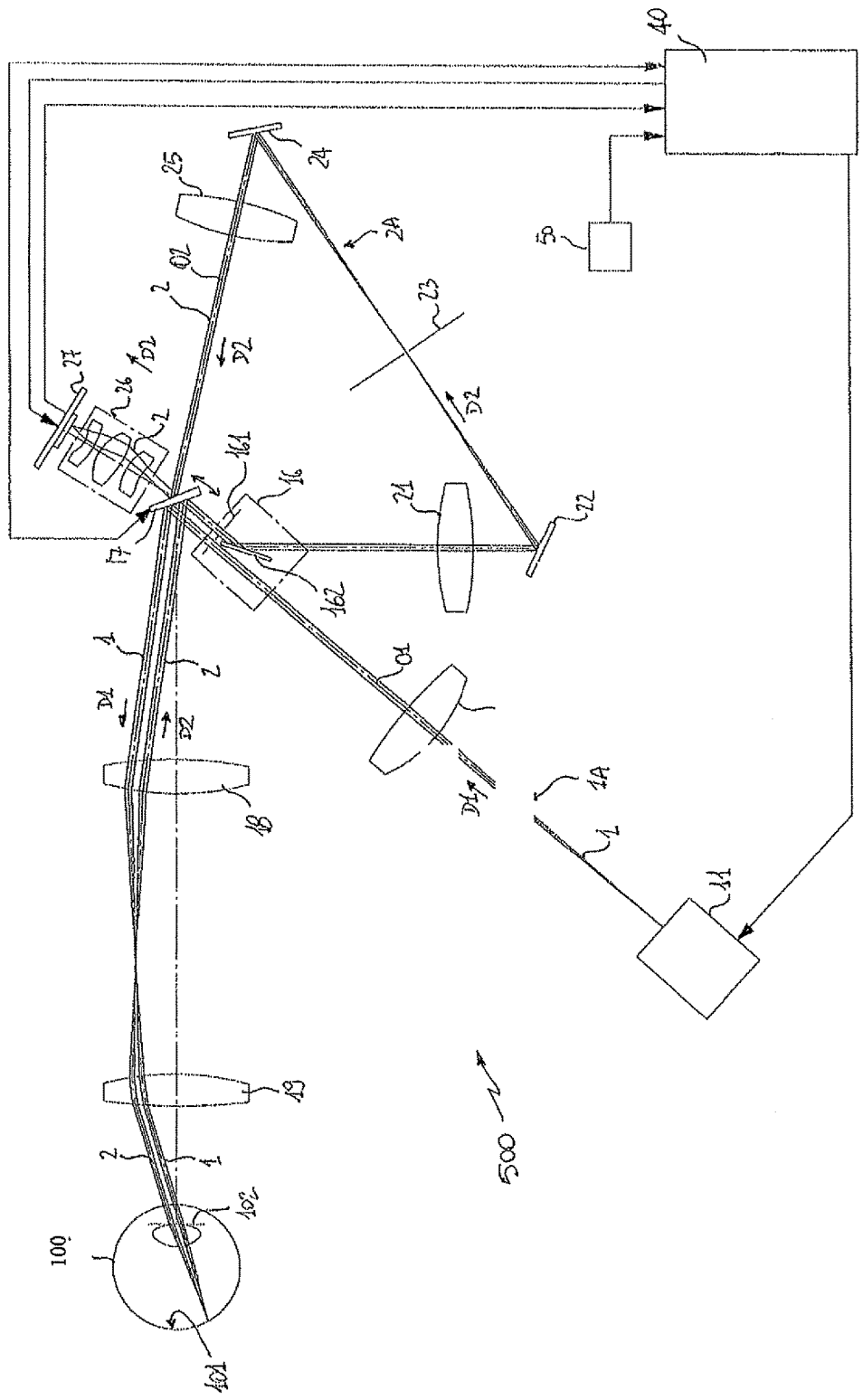
FIG. 1 schematically shows the eye examination apparatus according to the invention in a first embodiment thereof.

With reference to FIG. 1, the present invention relates to an eye examination apparatus 500.

The apparatus 500 comprises an illuminator 11 comprising at least a light source.

The apparatus 500 comprises an optical illumination path 1A, along which a light beam 1, projected by the illuminator 11, reaches the retina 101 of the eye 100. During the operation of the apparatus 1, the optical path 1A therefore extends from the illuminator 11 to the retina 101.

The illuminator 11 is arranged to project on the retina a light beam 1.

The light beam is shaped to form a line of light 1B that extends along a main axis of extension AE, when the light beam 1 intersects the retina (FIG. 8).

The apparatus 500 comprises image sensor 27 adapted to receive light 2 reflected by the retina 101 and to acquire one or more images of the same retina.

The apparatus 500 comprises an optical acquisition path (or optical imaging path) 2A, along which the light 2 reflected by the retina 101 reaches the image sensor 27. During the operation of the apparatus 1, the optical path 2A therefore extends from the retina 101 to the image sensor 27.

The apparatus 500 comprises scanning means 17 adapted to perform periodical optical scans of the retina 101. Each optical scan is performed by moving the light beam 1 projected by the illuminator 11 on the surface of the retina 101 along a scanning direction DS (FIG. 8).

Due to the scanning means 17, the line of light 1B projected by the illuminator 11 moves, during an optical scan, along the surface of the retina according to the scanning direction DS.

Preferably, the scanning means 17 also have the function of directing at least a portion of the light 2 reflected by the retina along the optical acquisition path 2A toward the image sensor 27.

The apparatus 500 comprises separation means of the light beams 16 adapted to separate the light 1 projected on the retina from the light 2 reflected by this latter and directed toward the image sensor 27.

The illuminator 11, the separation means of the light beams 16 and the scanning means 17 are advantageously arranged in series along the optical path 1A (with reference to the direction D1 of the light beam 1).

Preferably, the apparatus 500 comprises a first optics 15 arranged along the optical path 1A between the illuminator 11 and the separation means of the light beams 16.

Preferably, the apparatus 500 comprises a scanning optics 18 and an eyepiece 19, arranged downstream of the scanning means 17 (with reference to the direction of travel D1 of the light beam 1) along the optical path 1A, so as to be passed through by the illumination light 1.

The scanning means 17, the separation means of the light beams 16 and the image sensor 27 are advantageously arranged in series along the optical path 2A (with reference to the direction of travel D2 of the light beam 2).

The eyepiece 19 and the scanning optics 18 are also arranged along the optical path 2A and are passed through by the reflected light 2, before this latter reaches the scanning means 17.

Preferably, the apparatus 500 comprises a confocal diaphragm 23 arranged along the optical path 2A so as to be optically conjugated with the retina 101, during the operation of the apparatus 500.

For greater clarity of exposition, it is specified that, within the scope of the present invention, the definition "optically conjugated" identifies positioning in the exact position of optical conjugation or in a relatively small neighbourhood (with respect to the lengths of the optical paths of the apparatus 500) of the exact position of optical conjugation.

The confocal diaphragm 23 preferably comprises at least a confocal opening that allows the passage of a portion of the reflected light 2 and is capable of at least partially stopping the light reflected by some surfaces of the apparatus 500 or of the eye 100 that are not optically conjugated with the retina.

Preferably, the apparatus 500 also comprises a second optics 21, the mirrors 22, 24, a third optics 25, an objective 26 arranged along the optical path 2A, between the separation means of the beams 16 and the image sensor 27.

As will be more apparent below, the mirror 22 or 24 can be replaced by a beam splitter 220.

To produce the optical paths 1A, 2A construction variants that provide for the use of mirrors or diaphragms having configurations different from the one shown in the cited figures are possible.

Preferably, the illuminator 11 comprises at least a light source consisting of an LED device.

Preferably, the image sensor 27 consist of, for example, one or more two-dimensional CCD or C-MOS sensors of a digital video camera. The image sensor 27 receives the light 2 at a receiving surface and advantageously allows the retina 101 to be observed and filmed.

Preferably, the separation means of the light beams 16 comprise a separation diaphragm 161, optically conjugated with the pupil 102, during the operation of the apparatus 500.

Preferably, the separation means of the light beams 16 comprise a mirror 162 adapted to divert the reflected light 2 directed by the scanning means 17 along the optical path 2A.

Preferably, the scanning means 17 cyclically move the direction of reflection of the illumination beam between two end positions, hereinafter end-of-travel positions.

Preferably, the scanning means 17 comprise a resonant mirror oscillating around a rotation axis.

Preferably, the mirror 17 comprises two opposed reflecting surfaces.

Other construction solutions that, for example, provide for the use of a polygonal mirror, an array of micromirrors and the like, are possible.

For greater clarity of exposition, it should be specified that the scanning means 17 can also operate (i.e. perform repeated cyclic scanning movements, each between the aforesaid end-of-travel positions) when the illuminator 11 is deactivated, i.e. does not project light toward the retina 101.

When the scanning means 17 and the illuminator 11 are activated, the scanning means 17 perform one or more optical scans of the retina 101 moving the light beam 1 (preferably substantially in the shape of a line of light 1B) projected on the surface of the retina 101 along a scanning direction DS.

The general operation of the apparatus 500 (in the embodiment of FIG. 1) is now described in greater detail.

The light beam 1 projected by the illuminator 11 passes through the optics 15 and the separation means 16 of the light beams, in particular at an opening of the separation diaphragm 161.

The light 1 is scanned by the scanning means 17 that direct it toward the retina 101 moving around the rotation axis thereof. It passes through the scanning optics 18 and the eyepiece 19 and enters the eye 100 to illuminate the retina 101.

On the retina 101, the illuminated portion consists of the light image projected by the illuminator 11. This illuminated portion, in the shape of line of light 1B, moves along the retina according to a scanning direction DS set by the scanning means 17. The scanning direction DS is substantially perpendicular to the axis of extension AE of the line of light 1B.

The light 2 reflected by the retina 101 exits from the eye through the pupil 102 passes back through the eyepiece 19 and the scanning optics 18.

The reflected light 2 is de-scanned by the scanning means 17 that direct it along the optical path 2A.

The reflected light 2 passes through the separation means 16 of the light beams, in particular at an opening of the separation diaphragm 161. This opening selects the portion of reflected light 2 that passes through a predetermined region of the pupil 102 separated from the region of pupil through which the light beam 1 enters the eye.

This greatly reduces the probability of undesired reflections of the illumination light 1, coming from surfaces of the eye different from the retina, reaching the image sensor 27.

The light beam 2, selected by the separation means 16, passes through the optics 21, is reflected by the mirror 22, passes through the confocal diaphragm 23, is reflected by the mirror 24 and passes through the optics 25.

The passage of the light beam 2 through the confocal diaphragm 23 greatly reduces the probability of undesired reflections, coming from objects positioned in planes different from the retina 101 or optically conjugated with the same retina, reaching the image sensor 27.

The light beam 2 is once again scanned by the scanning means 17 and directed toward the image sensor 27 to form a two-dimensional image on the two-dimensional receiving surface of the image sensor 27.

The light beam 2 passes the objective 26 to reach the image sensor 27 that acquire one or more images of the retina 101.

The apparatus 500 also comprises a control unit 40 to control the operation of the apparatus 500, for example to perform signal acquisition, data storage, data calculation and control signal generation functions.

Preferably, the control unit 40 comprises a digital processing device, for example a microprocessor. For example, it can consist of a computer.

The control unit 40 is operatively associated with the illuminator 11, the scanning means 17 and the image sensor 27 and is capable of controlling their operation by generating suitable control signals.

To generate these control signals, the control unit 40 preferably executes suitable software instructions stored in one or more memory locations of the same control unit.

The control unit 40 can be operatively associated with a human-machine interface 50 for entering manual commands or for performing configuration or programming operations.

The control unit 40 is capable of controlling operation of the illuminator 11, of the scanning means 17 and of the image sensor 27 so that the scanning means 17 scan the light beam 1 projected by the illuminator 11 on the surface of the retina 101 (i.e. perform optical scans of the retina) with a higher frequency than the frequency with which the image sensor acquire the images of the same retina.

In particular, according to the invention, the control unit 40 is adapted to control the operation of the illuminator 11, of the scanning means 17 and of the image sensor 27 so that, in order to acquire each single image of a region of the retina to be framed, the image sensor 27 integrates light 2 reflected by the retina during at least two complete optical scans of the region of the retina to be framed by the scanning means 17.

For the sake of clarity, it is specified that the sentence "the image sensor 27 integrates light" means that the pixels of the image sensor 27 accumulate electric charge as an effect of the light exposure. The final electric charge stored by each pixel is a measure of the total light energy incident to said pixel from the beginning of the integration time to its end.

According to the present invention, the final electric charge of each pixel of the image sensor 27 is determined by the total amount of light energy received by said pixel during at least two complete optical scans of the retina.

The integration time of the image sensor 27 is therefore long at least as the time necessary to perform two complete optical scans of the region of the retina to be framed.

For the sake of clarity, it is further specified that a scan of the region of the retina to be framed is a "complete scan" when said region of the retina is scanned on its entire surface, from one end to another.

According to the invention, the image sensor 27 acquire each image of the region of the retina 101 to be framed with a higher exposure time (preferably an integer multiple) than the execution time of a sole optical scan of the retina by the scanning means 17.

During the exposure time of the image sensor 27 (i.e. the time required to acquire a single image), the region of the retina to be framed is scanned by the scanning means 17 at least twice, preferably an integer number of times greater than or equal to two.

Consequently, each image of said region of the retina is acquired by the image sensor 27 by integrating light reflected by the retina during at least two complete optical scans of the same region of the retina.

Typically the number of optical scans required to acquire each single image of the region of the retina to be framed can vary between a few scans (for example 3 or 4) and a few tens of scans (for example 30 or 40).

The solution proposed by the invention to control the exposure of the image sensor 27 during multiple scans of the retina allows the quantity of light (light energy), which come from the retina and is integrated by the image sensor 27, to be adjusted during the acquisition of an image.

For example, during the acquisition of an image, it is possible to adjust the quantity of light reflected by the retina by varying the integer number (greater than or equal to two) of optical scans that effectively contribute to the acquisition of the same image.

A further advantage of the solution proposed by the invention consists in the fact that it allows considerable flexibility of the method with which the apparatus 500 takes a video of the retina, for example illuminating this latter with infrared light.

In particular, the aforesaid video can be produced so as to obtain a higher frequency of the images acquired or so as to obtain better quality of these images.

This is possible by selecting the number of scans of the retina corresponding to each image acquired.

If a video with images at higher frequency is required, the images are acquired with an integration time that corresponds to a few optical scans of the retina and with higher gains. This acquisition method by the image sensor 27 can be useful if automatic detection of the movement of the eye is required.

Instead, if a video with a higher quality of images is required, acquisition is performed with smaller gains and with an exposure time of each image that corresponds to a larger number of optical scans of the retina. This acquisition method can be useful for in vivo observation of the retina.

The solution of varying the exposure time of the image sensor 27, by changing the corresponding number of optical scans that contribute to the acquisition of each image, can advantageously be used also when using economical scanning means with fixed scanning frequency, for example oscillating resonant mirrors, and illuminators having constant powers, simpler and less costly than illuminators with adjustable power.

Figure 2:
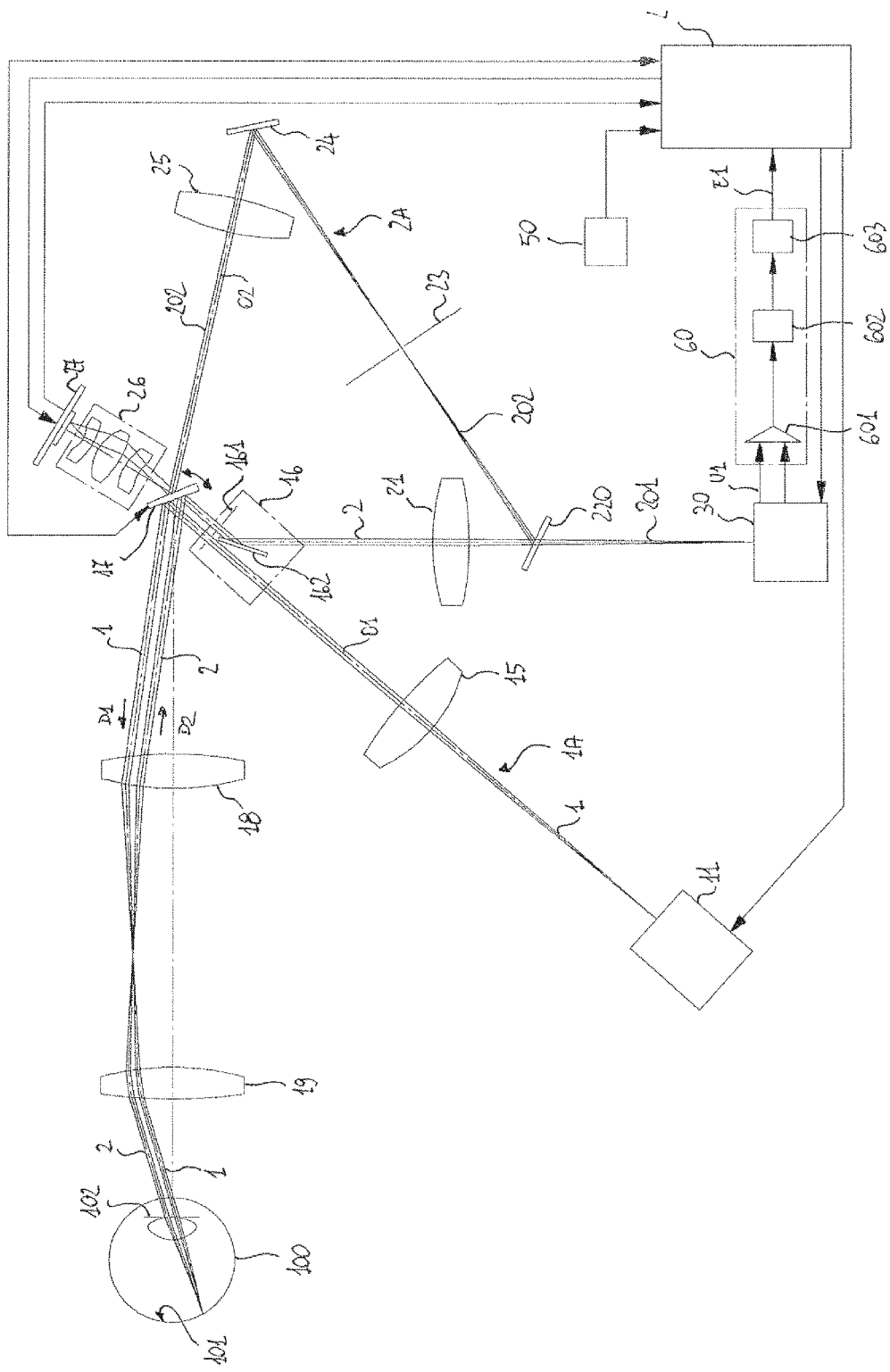
FIG. 2 schematically shows the eye examination apparatus according to the invention in a further embodiment thereof.
Figure 3:
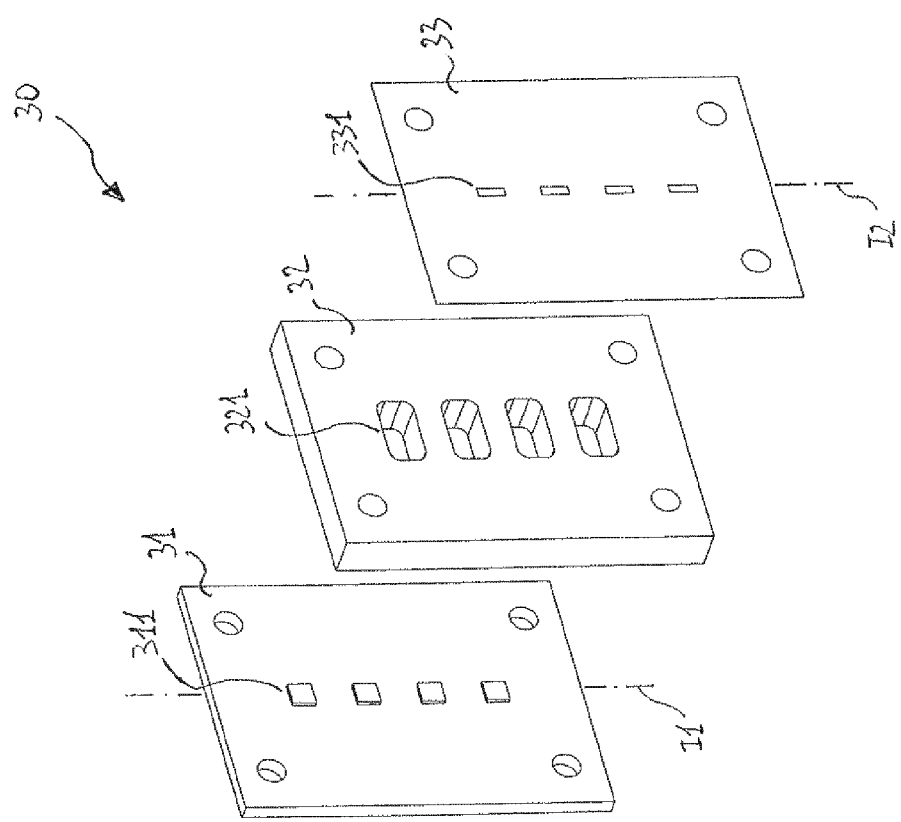
FIGS. 3-4 schematically show some details of the eye examination apparatus of FIG. 2.
Figure 4:
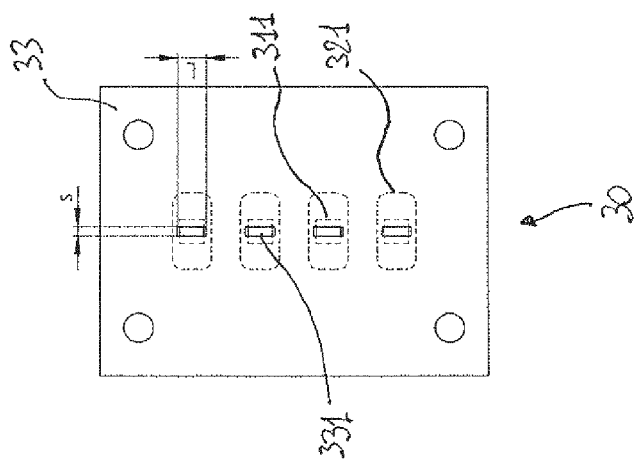
Figure 4:
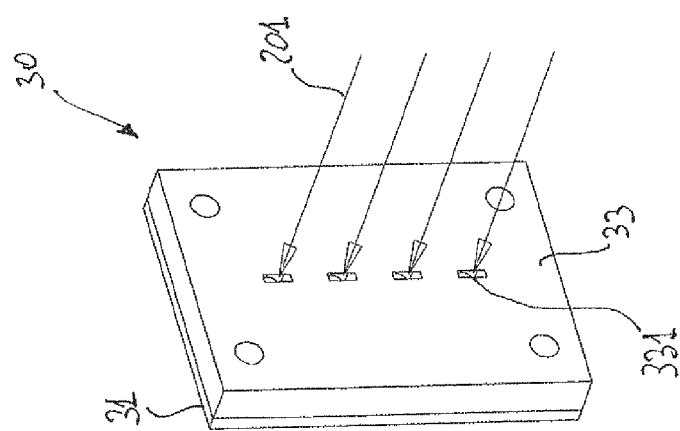

A further embodiment of the apparatus 500 is shown in FIG. 2.

According to this embodiment, the apparatus 500 comprises a light detection device 30 that comprises one or more photosensitive elements 311 and a beam splitter 220 adapted to divide the light 2 reflected by the retina and passing through the separation means 16 of the light beams (in particular through the separation diaphragm 161) into a first portion and a second portion 201, 202 of light reflected by the retina.

The beam splitter 220 is positioned along the acquisition path 2A, preferably between the optics 21 and the confocal diaphragm 23.

In practice, the beam splitter 220 replaces the mirror 22 present in the embodiment of the apparatus 500 shown in FIG. 1.

The beam splitter 220 directs the first portion 201 of light reflected by the retina toward the light detection device 30 and directs the second portion 202 of light reflected by the retina toward the image sensor 27.

The portion 202 of reflected light passes through the confocal diaphragm 23 that eliminates the undesired reflections, coming from objects positioned in planes different from the retina or optically conjugated with the same retina, continues encountering the mirror 24 and the optics 25, is scanned again by the scanning means 17 and is made to pass through the objective 26 to generate a two-dimensional image at the image sensor 27, which can thus acquire images of the retina.

The portion 201 of reflected light is directed toward the light detection device 30.

The detection device 30 comprises one or more photosensitive elements 311, each of which can, for example, be a photocell, a photo-transistor, an integrated light sensor or any other type of device adapted to provide an electrical detection signal U1 indicative of the light power received.

According to the embodiment of FIG. 2, the illuminator 11 does not have adjustable power and can be activated by the control unit 40 to project light only with predetermined constant power.

According to a possible variant of embodiment (not shown), the beam splitter 220 can be positioned downstream of the confocal diaphragm 23 (according to the direction D2 of the light reflected by the retina).

In this case, the beam splitter 220 replaces in practice the mirror 24 present in the embodiment of the apparatus 500 shown in FIG. 1.

In this variant of embodiment, the confocal diaphragm 23 stops the light coming from undesired reflections before the portion of reflected light 201 reaches the detection device 23. This ensures that the photosensitive elements 311 measure only the light reflected by the retina 101 and not light coming from undesired reflections.

Further variants of embodiment that provide for different positioning of the beam splitter 220 are possible.

Preferably, the detection device 30 comprises a support 31, for example a printed circuit board, on which the photosensitive elements 311 are mounted.

Preferably, the detection device 30 comprises a plurality of photosensitive elements 311, arranged on a plane defined by the support 31.

Preferably, the photosensitive elements 311 are arranged according to a first direction I1 which, during the operation of the apparatus 500, is optically conjugated with the main axis of extension AE of the line of light 1B projected by the illuminator 11 on the retina.

Preferably, the detection device 30 comprises a mask 33 optically conjugated with the retina during the operation of the apparatus 500.

The mask 33 comprises one or more openings 331 adapted to allow the passage of light toward the photosensitive elements 311.

Preferably, each of the openings 331 is operatively associated with a corresponding photosensitive element 311.

Preferably, the mask 33 comprises a plurality of openings 331.

Preferably, the openings 331 are arranged according to a second direction I2, which, during the operation of the apparatus 500, is optically conjugated with the main axis of extension AE of the line of light 1B projected by the illuminator 11 on the retina.

Preferably, the detection device 30 comprises an intermediate body 32 operatively positioned between the mask 33 and the support 31.

The intermediate body 32 comprises one or more cavities 321.

Preferably, the intermediate body 32 is operatively associated with the support 31 and with the mask 33 so that the cavities 321 allow the passage of light toward the photosensitive elements 311.

Preferably, one or more cavities 321 define one or more chambers adapted to enclose one or more photosensitive elements 311.

The number of chambers 321 can differ with respect to the number of photosensitive elements 311, for example in the case in which a plurality of photosensitive elements is grouped in the same chamber 321.

Preferably, as shown in FIGS. 3-6, each of the cavities 321 defines a chamber for a corresponding photosensitive element 311.

Advantageously, the chambers 321 protect the photosensitive elements 311 from external light and dust.

The support 31, the intermediate body 32 and the mask 33 can be easily assembled together with known fastening means.

According to a possible variant, the assembly composed of the mask 33 and of the intermediate body 32 can be produced in once piece.

In this case, the mask 33 is formed by a surface of the assembly adapted to receive the portion 201 of light reflected by the retina.

The cavities 321 and the openings 331 can be easily arranged so as to communicate with one another and allow the passage of light toward the photosensitive elements 311.

Advantageously, the detection device 30 is mounted on the apparatus 500 so that the mask 33 is located in a plane substantially conjugated with the retina 101 of the eye during the operation of the same apparatus.

As mentioned above, the photosensitive elements 311 and the openings 331 are arranged according to directions I1, I2 optically conjugated with the axis of extension AE of the line of light 1B projected by the illuminator 11 on the retina.

This ensures a high (theoretically the maximum possible) transfer of power from the illuminated region (the line of light 1B) of the retina to the photosensitive elements 311.

The dimension L of the openings 331, according to the direction I2, can be more or less the same or slightly larger than the dimension of the photosensitive elements 311 along the direction I1. This allows maximizing of the quantity of light 201 coming from the retina and traveling toward the photosensitive elements 311.

The dimension S of the openings 331 perpendicular to the direction I2, can be sufficiently limited to efficiently prevent the light coming from undesired reflections from reaching the photosensitive elements 311.

In this case, the mask 33 provided with openings 331 arranged according to the direction I2 operates as a confocal diaphragm operatively associated with the photosensitive elements 311. In this way, the photosensitive elements 311 substantially receive light coming from the retina and not light coming from undesired reflections on surfaces not conjugated with the same retina, for example the surfaces of the various lenses of the same apparatus or the surfaces of the front segment of the eye.

The detection device 30 provides output detection signals U1 generated by the photosensitive elements 311 when these latter are illuminated by the light beam 201.

This allows measuring of the light energy transmitted by the light beam 201 and, therefore, proportionally, the light energy of the light beam 202, i.e. the quantity of light reflected by the retina that reaches the image sensor 27.

When the retina is illuminated, each of the photosensitive elements 311 of the detection device 30 receives a portion of the light beam 201 and generates detection signals U1 indicative of the light power P of the beam 201 according to an operating characteristic thereof (FIG. 7).

Preferably, the apparatus 500 comprises signal conditioning means 60 adapted to receive the detection signals U1 from the photosensitive elements 311 and to provide measuring signals E1 indicative of the light energy received by the photosensitive elements.

Preferably, the signal conditioning means 60 comprise at least a summing means 601 to sum together the detection signals U1, an amplifier 602 to amplify the signal output from the summing means and an integrator 603 to integrate in time the signal output from the amplifier 62.

The order in which the summing means, the amplifier and the integrator operate can also differ from the order indicated in FIG. 2.

Preferably, the signal conditioning means 60 consist of one or more electronic circuits electrically connected between the detection device 30 and the control unit 40.

In this case, the signal conditioning means 60 are preferably integrated in the detection device 30 and mounted on the support 31 on which the photosensitive elements 311 are mounted.

According to alternative variants of embodiment, the signal conditioning means 60 could consist of a "stand-alone" electronic device or be mounted on the control unit 40.

According to a further alternative embodiment, the signal conditioning means 60 could consist of suitable software instructions that can be stored in and executed by the control unit 40 or by other computerized units capable of communicating with the control unit 40.

Preferably, the control unit 40 controls the operation of the illuminator 11 based on the measuring signals E1 provided by the signal conditioning means 60.

Preferably, the control unit 40 is configured to perform a first adjustment procedure of the quantity of light 202 (light energy) and received by the image sensor 27.

This adjustment procedure preferably comprises the following steps (not necessarily in the order set down below):
providing control signals to activate the illuminator 11 and the image sensor 27, when the scanning means 17 are in proximity of an end-of-travel position;
acquiring the measuring signal E1;
comparing the measuring signal E1 with a threshold value ETH;
if the measuring signal E1 has values higher than the threshold value ETH, waiting for completion of the optical scan of the retina in progress;
providing control signals to deactivate the illuminator 11, when the optical scan in progress is completed.

During the operation of the apparatus 500, the scanning means 17 can continuously perform scanning movements (for example oscillating around the rotation axis thereof) even if the illuminator 11 is deactivated.

After receiving a command to acquire an image, for example by means of the human-machine interface 50, the control unit 40 waits for the time required for the scanning means 17 to reach the end-of-travel of the scanning movement in progress.

When the scanning means 17 reach their end-of-travel (and therefore must start a new scanning movement), the control unit generates control signals to activate the illuminator 11 (so as to project light toward the retina and perform multiple optical scans thereof) and to activate the image sensor 27 (so as to start acquisition of an image of the retina).

The photosensitive elements 311 are illuminated by the light beam 201 and provide detection signals U1 indicative of the light power received.

The signal conditioning means 60 receive the detection signals U1 and provide measuring signals E1 indicative of the light energy received by the photosensitive elements 311.

The measuring signals E1 are acquired by the control unit 40.

When the light energy received by the photosensitive elements 311 exceeds the threshold ETH, the control unit 40 waits until the scanning means 17 complete the N-th (N>=2) optical scan in progress reaching an end-of-travel position.

When the scanning means 17 reach their end-of-travel position (and they must therefore start a new scanning movement), the control unit 40 generates control signals to deactivate the illuminator 11.

The solution described above has considerable operating advantages.

It allows synchronization of the start and end of the exposure period of the image sensor 27 with the movements of the scanning means 17, in particular with the end-of-travel moments of these latter.

In this way, the receiving surface of the image sensor 27 is exposed uniformly to the light reflected by the retina, i.e. for a time corresponding to the same number of optical scans.

If the start or the end of the exposure period of the image sensor 27 takes place randomly, not synchronized with the movements of the scanning means 17, a portion of the receiving surface of the image sensor 27 could be exposed for a number N of optical scans while the remaining receiving surface could be exposed for a number N+1 or N−1 of optical scans. In this case, the resulting image of the retina could comprise lighter regions and darker regions.

It can be seen how, in the adjustment procedure described above, the integration time of the detection signals U1 (by the signal conditioning means 60) varies automatically as a function of the reflectivity of the retina.

For example, if a retina with low reflectivity is filmed, the signal U1 generated by the photosensitive elements 311 is of relatively low intensity and therefore a longer integration time is necessary to reach the predefined threshold ETH and deactivate the illumination means 11.

The exposure time of the image sensor 27 (in general corresponding to the time in which the retina is illuminated by the illuminator 11) thus varies in a manner inversely proportional to the reflectivity of the retina.

The quantity of light 201 that reaches the photosensitive elements 311 is therefore maintained substantially constant irrespective of the effective reflectivity of the retina.

As this quantity of light is substantially proportional to the quantity of light (light energy) that reaches the image sensor 27, also the quantity of light that reaches the image sensor 27 is maintained substantially constant at an adjustable value.

This allows images with substantially constant light exposure to be acquired, irrespective of the reflectivity of the retina examined.

Based on the above, it is evident how the detection device 30, the signal conditioning means 60 and the control unit 40 form means to adjust the light exposure of the image sensor 27.

In the adjustment procedure described above, the exposure of the image sensor 27 takes place by illuminating the retina for an integer number N of optical scans (N≥2) by means of an illuminator 11 with a constant light power.

Consequently, the resolution for adjustment of the light energy is equal to the quantity of light energy received by the image sensor 27 during an optical scan.

The adjustment precision of the light energy depends on the number N of optical scans performed to acquire an image.

The maximum theoretical error of the adjustment procedure described above is therefore equal to 1/N in which N is the number of optical scans completed to acquire the same image. For example, if the exposure time required to acquire an image corresponds approximately to 20 optical scans, the maximum adjustment error corresponds to one scan in every 20, i.e. to 5%.

A variant of the embodiment of the invention shown in FIG. 2 provides for the use of an illuminator 11 having adjustable light power.

The light power of the illuminator 11 can be adjusted by the control unit 40 by sending suitable control signals.

In principle, also in this case, the control unit 40 could perform the first adjustment procedure described above to adjust the quantity of light received by the image sensor 27.

Preferably, however, the control unit 40 is configured to perform a second adjustment of the quantity of light 202 received by the image sensor 27.

This adjustment procedure preferably comprises the following steps (not necessarily in the order set down below):
providing control signals to activate the illuminator 11 with a given power value (for example a maximum power value) and to activate the image sensor 27, when the scanning means 27 are in proximity of an end-of-travel position;
acquiring the measuring signal E1 after the scanning means 17 have performed a first number N1 of optical scans of the retina, with N1 positive integer;
comparing the measuring signal E1 with a threshold value ETH;
calculating a second number N2 of optical scans still to be performed in the case in which the illuminator 11 is adjusted to a new power value, with N2 positive integer;
providing control signals to change the power of the illuminator 11 to the new power value, when the scanning means 17 are in proximity of an end-of-travel position;
waiting for completion of the N2 optical scans of the retina by the scanning means 17;
providing control signals to deactivate the illuminator 11 when the N2-th optical scan of the retina is completed.

The adjustment procedure described above, together with the use of an illuminator with adjustable light power, allows significant improvement of the adjustment precision of the quantity of light 202 reaching the image sensor 27.

In fact, in this case the adjustment resolution does not depend on the number of optical scans performed.

With the adjustment procedure described above, it is possible to obtain good adjustment of the quantity of light 202 reaching the image sensor 27 even if the scanning means 17 only perform two optical scans during acquisition of an image of the retina (i.e. in the case in which N1=1, N2=1).

If only two optical scans are to be performed (minimum number possible), the control unit 40 can acquire the measuring signal E1 after the scanning means 17 have performed the first optical scan of the retina and compare the measuring signal E1 with a threshold value ETH.

The control unit 40 can then calculate the power with which the illuminator 11 must operate during the second optical scan to reach the energy threshold ETH.

To perform the adjustment procedures described above, the control unit 40 can advantageously perform, by means of its digital processing unit, software instructions stored in suitable memory locations.

According to a variant of the embodiment of the invention shown in FIG. 2 (FIGS. 5-6), the detection device 30 comprises one or more emitters 312 operatively associated with the photosensitive elements 311.

The emitters 312 are adapted to project light on the photosensitive elements 311.

The number of emitters 312 can differ with respect to the number of photosensitive elements 311, for example in the case in which a same emitter 312 projects light on several photosensitive elements 331.

Figure 5:
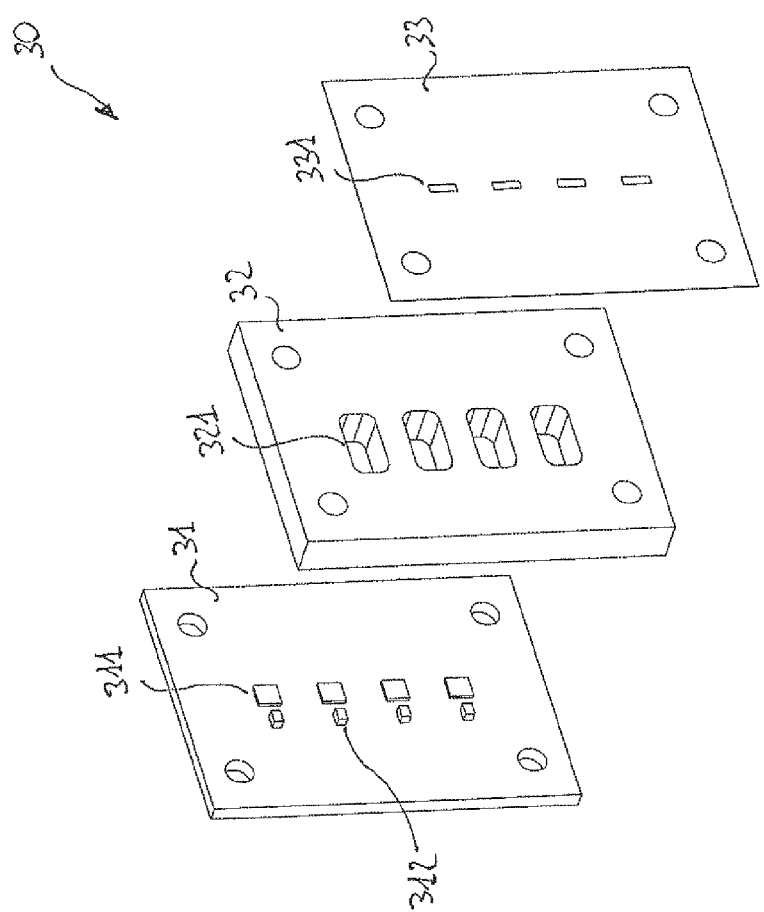
FIGS. 5-6 schematically show some details of the eye examination apparatus of FIG. 2 in a further variant of embodiment thereof.
Figure 6:
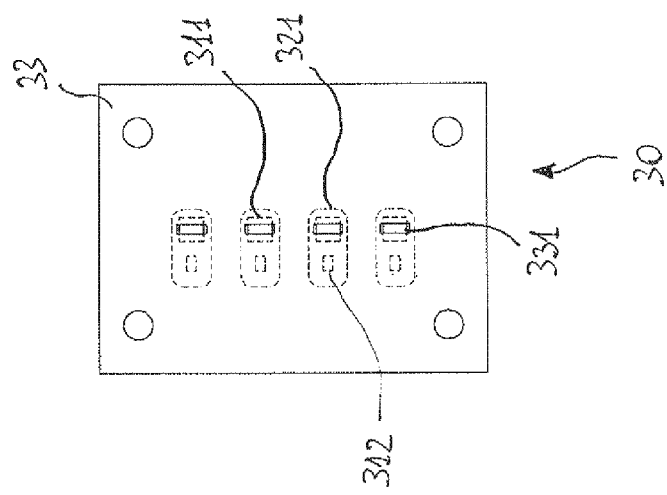
Figure 6:
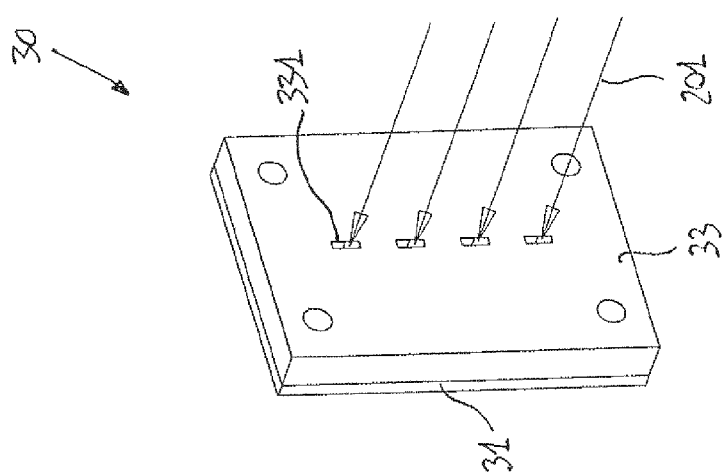

Preferably, as shown in FIGS. 5-6, each emitter 312 is operatively associated with a corresponding photosensitive element 311.

Preferably, the emitters 312 consist of LED devices.

According to this variant of embodiment, the mask 33 and the intermediate body 32 have characteristics substantially the same as those already described.

Preferably, the emitters 312 and the photosensitive elements 311 are mounted on the support 31 and are enclosed in the corresponding chambers defined by the cavities 321 of the intermediate body 32.

According to this variant of embodiment, the operation of the signal conditioning means 60 and of the control unit 40 is substantially the same as already described.

Preferably, the control unit 40 is capable of controlling the operation of the emitters 312 by means of suitable control signals.

Preferably, the control unit 40 activates the emitters 312, when the illuminator 11 and the image sensor 27 are activated by the same control unit.

In this way, the emitters 312 project light on the photosensitive elements 311 when the illuminator 11 and the image sensor 27 are activated, in other words, for the whole of the time in which the photosensitive elements 311 receive the light 201 reflected by the retina and generate the detection signals U1.

The solution described above has the advantage of making it possible to use economical light sensors (typically available on the market), even if characterized by a low precision in the case of very low incident light power.

A typical example of operating characteristic curve of an economical light sensor is shown in FIG. 7.

The operating characteristic curve of the sensor U1=f(P), in which U1 is the electrical signal (detection signal) generated by the sensor illuminated with a light power P, is linear for a range of light powers greater than a threshold value PTH.

If this threshold value is greater than the light power P1 of the light beam 201, the operating point of the sensor is located in a nonlinear region of the operating characteristic.

Consequently, a variation of reflectivity of the retina will not have as effect a proportional variation of the detection signal U1 provided by the sensor.

This means that the quantity of light, to which the image sensor 27 is exposed to acquire the images of the retina, might not be adjustable to a desired constant value.

It was also found that the sensor is characterized by high sensitivity to temperature variations, when operating in a nonlinear region corresponding to very low light powers.

This can cause substantial errors in the measurement of the light energy provided by the light beam 201.

Using the emitters 312, an additional quantity of constant light P2 can be projected on the photosensitive elements 311.

The total power (P1+P2) received by the photosensitive elements 311 can advantageously be selected so as to ensure that these latter always operate in a linear region of their operating characteristic, at which they are less sensitive to temperature variations.

In this way, it is possible to precisely measure the light power P1 provided by the light beam 201 and consequently to precisely adjust the quantity of light received by the image sensor.

The apparatus 1 according to the invention has considerable advantages with respect to prior art.

The fact that the image sensor 27 integrates light reflected by the retina for at least two optical scans of the same retina to produce an image advantageously allows:
- adjustment of the quantity of light used to acquire each image, suitably adjusting the number of optical scans that contribute to the acquisition of the aforesaid image;
- adjustment of the exposure time during acquisition of the videos, even if the scanning means 17 are capable of operating with fixed scanning frequency (and as such are economical).

The apparatus 500 is capable of automatically adjusting the quantity of light 202 received by the image sensor 27, for example by means of the adjustment procedures described above. This makes it possible to:
- obtain images with uniform brightness, irrespective of the variations of reflectivity of the retina examined;
- improve the signal/noise ratio of the images acquired in conditions with retinas with low reflectivity;
- avoid saturation of the images acquired in conditions with retinas with high reflectivity.

The use of the detection device 30 makes it possible to obtain a good precision of adjustment of the quantity of light received by the image sensor 27, efficiently reducing, making use of the confocality of the openings 331, the optical disturbance caused by reflections that could interfere with the energy measurement of the light beam 201.

The use of the emitters 312 adapted to project light on the luminous elements 311 during acquisition of the image of the retina makes it possible to:
- use low cost economical photosensitive elements maintaining a good level of precision of adjustment of the quantity of light received by the image sensor 27;
- reduce, by means of the beam splitter 220, the quantity of light 201 to be directed toward the detection device 30 and increase the quantity of light 202 to be directed toward the image sensor 27 and to be used to acquire an image, thus improving the quality of the same image;
- reduce the measuring errors due to temperature variations of the photosensitive elements 311 during measuring.

The apparatus 500 has a very compact structure and is easy to produce on an industrial scale, with considerable advantages in terms of limiting production costs.

The invention claimed is:

1. An eye examination apparatus comprising:
   an illuminator adapted to project a light beam in an eye to illuminate a portion of a retina, said light beam being shaped to form a line of light that extends along a main axis of extension across a surface of the retina, when said light beam intersects the retina;
   an image sensor adapted to receive light reflected by the retina and to acquire images of the retina;
   scanning means adapted to perform optical scans of the retina by cyclically moving the light beam projected by said illuminator on the retina along a scanning direction substantially perpendicular to the main axis of extension of said line of light;

separation means of the light beams adapted to separate the light projected by said illuminator from the light reflected by the retina and directed toward said image sensor; and a control unit to control the operation of said scanning apparatus;

wherein, in operation, to acquire each single image of a region of the retina to be framed, said image sensor integrates light reflected by the retina during at least two complete optical scans of said region of the retina by said scanning means.

2. The apparatus of claim 1, wherein, in operation, to acquire each single image of a region of the retina to be framed, said image sensor integrates light reflected by the retina during an integer number of complete optical scans of said region of the retina by said scanning means.

3. The apparatus of claim 1, further comprising:
a light detection device comprising at least a photosensitive element adapted to provide at least a detection signal indicative of the received light power; and
a beam splitter adapted to divide the light reflected by the retina and passing through said separation means of the light beams into a first and second portion of reflected light, said beam splitter directing said first portion of reflected light toward said light detection device and said second portion of reflected light toward said image sensor.

4. The apparatus of claim 3, wherein said light detection device comprises a mask optically conjugated with the retina during the operation of said apparatus, said mask comprising at least an opening adapted to allow the passage of light toward said at least a photosensitive element.

5. The apparatus of claim 4, wherein said light detection device comprises at least two photosensitive elements arranged according to a first direction, said mask comprising at least two openings arranged according to a second direction, said first and second direction being optically conjugated, during the operation of said apparatus, with the main axis of extension of the line of light projected by said illuminator on the retina.

6. The apparatus of claim 4, wherein said light detection device comprises:
a support on which said at least a photosensitive element is mounted;
an intermediate body provided with at least a cavity, said intermediate body being operatively associated with said support and with said mask so that said at least a cavity communicates with at least an opening of said mask to allow the passage of light toward said at least a photosensitive element and defines a chamber for said at least a photosensitive element.

7. The apparatus of claim 3, wherein said light detection device comprises at least an emitter operatively associated with said at least a photosensitive element, said at least an emitter being adapted to project light on said at least a photosensitive element.

8. The apparatus of claim 7, wherein, in operation, said at least an emitter projects light on said at least a photosensitive element, when said illuminator projects a light beam on the retina and said image sensor receives light reflected by the retina.

9. The apparatus of claim 3, further comprising signal conditioning means adapted to receive at least a detection signal from said at least a photosensitive element and to provide at least a measuring signal indicative of the light energy received by said at least a photosensitive element.

10. The apparatus of claim 9, wherein said control unit is adapted to control the operation of said illuminator based on said at least a measuring signal.

11. The apparatus of claim 10, wherein said control unit performs, during the operation of said apparatus, a first adjustment procedure of the quantity of light integrated by said image sensor, said first adjustment procedure comprising the following steps:
providing control signals to activate said illuminator and said image sensor when said scanning means are in proximity of an end-of-travel position;
acquiring said measuring signal;
comparing said measuring signal with a threshold value;
if said measuring signal has values higher than said threshold value, waiting for completion of the optical scan of the retina in progress;
generating control signals to deactivate said illuminator when the optical scan in progress is completed.

12. The apparatus of claim 10, wherein said at least an illuminator is adjustable in power, said control unit performing, during the operation of said apparatus, a second adjustment procedure of the quantity of light integrated by said image sensor, said second adjustment procedure comprising the following steps:
generating control signals to activate said illuminator, with a light power value and to activate said image sensor, when said scanning means are in proximity of an end-of-travel position;
acquiring said measuring signal after said scanning means have performed a first number of optical scans of the retina;
comparing said measuring signal with a threshold value;
calculating a second number of optical scans still to be performed in the case in which said illuminator is set to a new value of light power;
generating control signals to change the light power of said illuminator to said new value of light power, when said scanning means are in proximity of an end-of-travel position;
waiting for completion of said second number of optical scans of the retina;
generating control signals to deactivate said illuminator when said second number of optical scans of the retina is completed.

13. The apparatus of claim 1, wherein said scanning means comprise an oscillating resonant mirror.

14. An eye examination apparatus comprising:
an illuminator adapted to project a light beam in an eye to illuminate a portion of a retina, said light beam being shaped to form a line of light that extends along a main axis of extension across a surface of the retina, when said light beam intersects the retina;
an image sensor adapted to receive light reflected by the retina and to acquire images of the retina;
a resonant mirror oscillating around a rotation axis and adapted to perform optical scans of the retina by cyclically moving the light beam projected by said illuminator on the retina along a scanning direction substantially perpendicular to the main axis of extension of said line of light; and
a separation diaphragm of the light beams adapted to separate the light projected by said illuminator from the light reflected by the retina and directed toward said image sensor;

wherein, in operation, to acquire each single image of a region of the retina to be framed, said image sensor integrates light reflected by the retina during at least two complete optical scans of said region of the retina.

15. The apparatus of claim 14, further comprising:
a light detection device comprising at least a photosensitive element adapted to provide at least a detection signal indicative of the received light power; and
a beam splitter adapted to divide the light reflected by the retina and passing through said separation diaphragm into a first and second portion of reflected light, said beam splitter directing said first portion of reflected light toward said light detection device and said second portion of reflected light toward said image sensor.

16. The apparatus of claim 15, wherein said light detection device comprises a mask optically conjugated with the retina during the operation of said apparatus, said mask comprising at least an opening adapted to allow the passage of light toward said at least a photosensitive element.

17. The apparatus of claim 16, further comprising a control unit adapted to control the operation of said illuminator based on at least a measuring signal indicative of light energy received by said at least a photosensitive element.

18. The apparatus of claim 17, wherein said control unit performs, during the operation of said apparatus, a first adjustment procedure of the quantity of light integrated by said image sensor, said first adjustment procedure comprising the following steps:
providing control signals to activate said illuminator and said image sensor when a cyclic scanning movement is in proximity of an end-of-travel position;
acquiring said measuring signal;
comparing said measuring signal with a threshold value;
if said measuring signal has values higher than said threshold value, waiting for completion of the optical scan of the retina in progress;
generating control signals to deactivate said illuminator when the optical scan in progress is completed.

19. The apparatus of claim 17, wherein said at least an illuminator is adjustable in power, said control unit performing, during the operation of said apparatus, a second adjustment procedure of the quantity of light integrated by said image sensor, said second adjustment procedure comprising the following steps:
generating control signals to activate said illuminator, with a light power value and to activate said image sensor, when said scanning means are in proximity of an end-of-travel position;
acquiring said measuring signal after a first number of optical scans of the retina have been performed;
comparing said measuring signal with a threshold value;
calculating a second number of optical scans still to be performed in the case in which said illuminator is set to a new value of light power;
generating control signals to change the light power of said illuminator to said new value of light power, when a cyclic scanning movement is in proximity of an end-of-travel position;
waiting for completion of said second number of optical scans of the retina; and
generating control signals to deactivate said illuminator when said second number of optical scans of the retina is completed.

* * * * *